United States Patent [19]

Baisch et al.

[11] Patent Number: 4,751,186

[45] Date of Patent: Jun. 14, 1988

[54] PROCESS FOR PERFORMING SAMPLE ANALYSES AND RACK FOR PERFORMING THE PROCESS

[75] Inventors: Manfred Baisch; Horst Rüsbüldt, both of Hamburg, Fed. Rep. of Germany

[73] Assignee: Eppendorf Geratebau Netheler & Hinz GmbH, Hamburg, Fed. Rep. of Germany

[21] Appl. No.: 702,253

[22] Filed: Feb. 15, 1985

[30] Foreign Application Priority Data

Feb. 15, 1984 [DE] Fed. Rep. of Germany ....... 3405292

[51] Int. Cl.⁴ .................. G01N 1/10; G01N 21/00; G01N 35/02
[52] U.S. Cl. ........................................ 436/47; 422/65; 422/67; 422/102; 422/104; 356/246; 141/130; 211/162
[58] Field of Search ................... 422/65, 67, 102, 104, 422/64, 61; 436/47; 356/246; 141/130; 211/162

[56] References Cited

U.S. PATENT DOCUMENTS

| 3,582,285 | 6/1971 | Hamilton | 422/61 |
| 3,713,985 | 11/1973 | Astle | 422/102 |
| 3,753,657 | 8/1973 | Downing et al. | 422/65 |
| 3,759,374 | 9/1973 | Helger et al. | 356/246 |
| 3,905,772 | 9/1975 | Hartnett et al. | 422/102 |
| 3,916,157 | 10/1975 | Roulette et al. | 422/65 |
| 3,948,606 | 4/1976 | Johnson | 422/104 |

Primary Examiner—Barry S. Richman
Assistant Examiner—Lynn Kummert
Attorney, Agent, or Firm—Lane & Aitken

[57] ABSTRACT

A process for performing sample analyses wherein reagents are filled portionwise into closed containers that comprise cells and carry codes identifying the reagent contained therein. Cells required for different analyses are placed in a rack together with a sample container containing the sample. A code identifying the sample is applied to the rack. The codes on the cells and the code on the rack are read with the same reading unit.

5 Claims, 1 Drawing Sheet

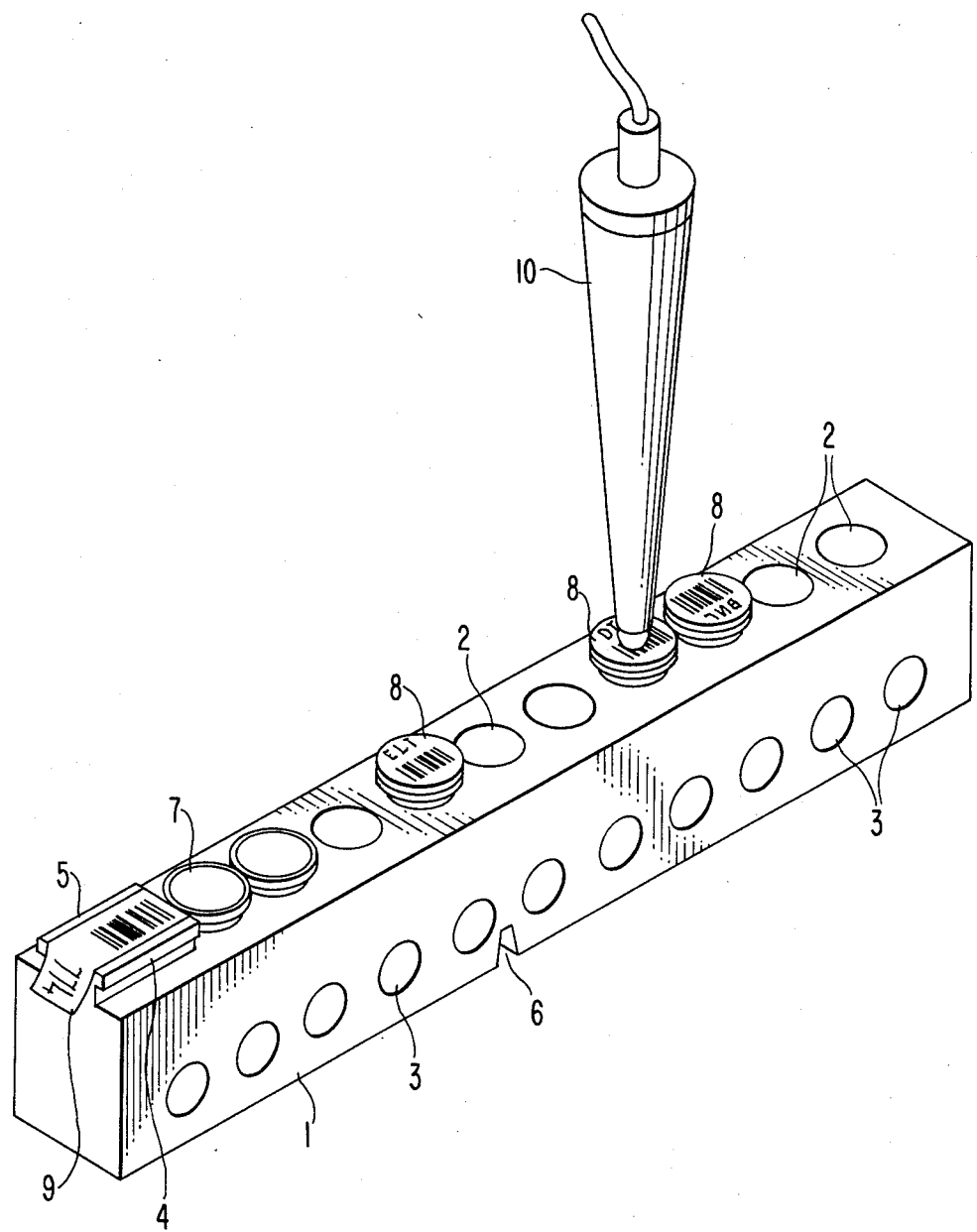

PROCESS FOR PERFORMING SAMPLE ANALYSES AND RACK FOR PERFORMING THE PROCESS

BACKGROUND OF THE INVENTION

1. Field of the Invention

This invention relates to a process for performing sample analyses, in which parts of a sample and optionally solvents and reagents are added in portionwise manner into closed containers carrying a code identifying the reagent. The reaction processes which occur are photometrically measured and the results are indicated and/or printed out, together with a sample identification.

2. Description of the Prior Art

In connection with a known process of this type, Du Pont de Nemours (Deutschland) GmbH markets under the trade name "aca SYSTEM" an analyzer enabling various clinical analyses to be performed on a sample fluid taken from a patient. A reagent container with the corresponding reagents is selected for each of the analyses to be performed. These reagent containers comprise a plastic bag having various closed reception areas for reagents and a flexible cuvette or cell area. The bag is hung on a clip, which carries a code identifying a reagent contained in the bag. The sample fluid is filled into a sample container and a card identifying the patient is associated with said container. The sample container, including the card and the reagent containers necessary for the various tests, are then introduced into the analyzer and the reaction process is started. In said analyzer, sample fluid from the sample container and in each case reagent and optionally solvent are brought into the vicinity of the flexible cell and the reaction process of the particular test is photometrically measured. Following the performance of all the analyses, the analyzer prints out the analytical data, together with a patient identification.

Despite partial automation, this known process is relatively costly from the labor standpoint, because the operator must introduce into the analyzer the sample container, the card identifying the patient and the reagent containers necessary for each individual analytical process.

The problem of the present invention is to considerably simplify an analytical process and in particular to obviate the need for the filling and identification operations relative to the partial samples hitherto required for performing different analyses on a sample.

SUMMARY OF THE INVENTION

In connection with a process of the aforementioned type, according to the invention this problem is solved in that a sample container, together with the containers containing the necessary reagents in the form of cells, are placed in the reception openings of a rack. A code identifying the sample is applied to the rack and codes identifying the reagents are applied to the cells. The codes on the cells and the code on the rack are read by means of the same reading unit.

Thus, in the process according to the invention, the reagents for the different analyses of a sample are housed in one rack, which also receives the sample container. A sample-identifying code is applied to the rack and, in one embodiment, is fixed beforehand to sample containers supplied. Thus, the individual sample containers and all the cuvettes or cells with the reagents required for the analyses to be performed are combined into one unit in the rack and it is merely necessary to apply a single sample-identifying code to the rack, in order to associate the analytical data to be indicated, displayed and/or printed out with the analyzed sample. The codes on the cells and the code on the rack are read with the same reading unit, so that apparatus expenditure is also extremely small.

According to a preferred development of the inventive process, the codes are placed on the closures of the cells and on the upper surface of the rack and, by movement in the direction of its longitudinal extension, the rack is moved under the head of the reading unit.

The placing of codes on the closures of the cells provides the advantage that incorrect fillings can be avoided in a simple manner, because the code is only associated with the cell following the filling thereof. In addition, the cells with all their body part located beneath the closure are positioned in the rack, so that a stable and clearly defined positioning of the cell and in particular the coding thereof on the container closure is ensured and this largely eliminates reading errors.

The invention also relates to a rack with reception openings for cells and openings for the passage of test radiation for the photometric measurement of the reaction processes in the cells. For the performance of the process according to the invention, this rack comprises a reception surface for a code, which is located in substantially the same plane with the codes provided on the inserted cells, so that the codes of the cells and the code on the rack can be moved past the reading unit head, without the position of the head having to be modified on changing over from reading the cell code to reading the rack code.

If cells are used in which the codes are on the top surfaces of the closures, then the reception surface on the top of the rack is raised with respect to the remainder of the top surface and is also flat. The reception surface is then located at one end of the rack.

BRIEF DESCRIPTION OF THE DRAWING

FIG. 1 is a perspective view of an apparatus suitable for use in the present invention.

DESCRIPTION OF THE PREFERRED EMBODIMENTS

The invention is explained in greater detail hereinafter relative to FIG. 1 which shows a filled rack and the head of a reading unit.

The represented rack 1 comprises an elongated, cross-sectionally substantially rectangular metal body, along whose median longitudinal plane are formed upwardly open reception openings 2, which are used both to receive a sample container 7 and also cells 8, which contain reagents and which are closed. As indicated, the cell closure covering surfaces carry bar codes identifying the reagent in the particular cell. The reception openings 2 are shaped in such a way that the cells 8 can only be inserted in rack 1 in such a way that their optical faces to be transilluminated for the measurement of the reaction processes are located in the area of the bores 3 extending at right angles through rack 1, it being obvious that one bore 3 is associated with each reception opening 2.

On the top surface at one end of the rack is provided a raised portion 4, which is constructed in one piece with the remainder of the body of rack 1. The upper surface 5 of raised portion 4 is flat and is substantially in one plane with the upper surfaces of the container closures of the cells 8 inserted in the rack. It is pointed out that the upper surface of sample container 7 does not project upwards above said plane.

A code 9 identifying the sample in sample container 7 is applied to surface 5. As shown, said code firstly comprises a bar code located in the plane of the codes on the closures of cell 8 and secondly a number designating the sample and located on the rear face of rack 1.

In order to perform a sample analysis, the sample container 7 containing the sample is placed in rack 1 and the sample-identifying code 9 is attached to the rack. The cells 8 which contain the reagents required for the different analyses are inserted in reception openings 2. The thus prepared rack is placed in a corresponding analyzer, where there is firstly a thermostatic control, such as is for example described in related German patent application No. P 34 05 293.3, which corresponds to the U.S. application of Manfred Baisch, Horst Rusbuldt, and Manfred Knaus, entitled "Process for the Thermostatic Control of a Sample Fluid to be Analyzed, As Well As of Reagents for Performing Analyses and Apparatus for Performing the Process," Ser. No. 702,252 filed on Feb. 15, 1985, which is hereby incorporated by reference. Partial samples are then sucked out of the sample container 7 and, through the perforation of the closure of the particular cell 8, are introduced into the latter and optionally solvent can also be added. In order to perform this filling operation, the rack 1 is correspondingly reciprocated in the direction of its longitudinal extension by the engagement of a cam in recess 6.

The control of the movement sequence both for introducing the partial samples in the various cells 8 and for the movement of a bore 3 in the area of the optical path used for measuring the reaction process, including the association of the measured result with the particular analysis, takes place by means of a reading unit, under whose head 10 are passed the codes on the closures of cells 8, in order in this way to read said codes and identify the particular reagent and the analysis to be performed, whilst also controlling the following movement sequence for rack 1. A clearly defined association of these analytical data with the analyzed sample contained in the sample container 7 is also obtained through reading code 9 when the said data are indicated, displayed and/or printed out.

We claim:

1. An automated process for performing sample analyses comprising the steps of providing a rack having a means for holding containers, filling with reagents a plurality of reagent containers having means for allowing radiation to pass therethrough for making photometric measurements, closing said plurality of reagent containers, and applying a code identifying a contained reagent to a reagent-code-receiving surface of each of said plurality of reagent containers, placing said plurality of reagent containers and at least one sample container containing a sample to be analyzed in said rack, applying a code identifying said sample to a sample-code-receiving surface of said rack, such that all of said code-receiving surfaces are disposed in substantially the same plane, removing portions of said sample from said at least one sample container and introducing said sample portions into said plurality of reagent containers, passing radiation through said plurality of reagent containers into which said sample portions have been introduced to make photometric measurements, and passing the sample code and the reagent codes applied to said rack and said plurality of reagent containers, respectively, beneath a reading unit to associate said measurements with said reagent and sample codes.

2. The process of claim 1, wherein said reagent codes are applied to closures of said plurality of reagent containers and said sample code is applied to an upper face of said rack, and wherein said passing step comprises moving said reagent codes and said sample code beneath the head of the reading unit by movement in a direction of a longitudinal axis of said rack.

3. The process of claim 1, further comprising the step of placing a solvent associated with one of said reagents in a container and placing said solvent container in said rack.

4. A kit for automatically performing sample analyses comprising a rack for holding a plurality of discrete, closed containers, said rack comprising a sample-code-receiving surface provided with a code identifying a sample to be analyzed, at least one sample container for containing the sample, a plurality of closed reagent containers containing reagents into which portions of the sample are to be introduced, said plurality of reagent containers each comprising a reagent-code-receiving surface provided with a code identifying a respective reagent contained therein, wherein said surfaces of said plurality of reagent containers protrude above an upper surface of said rack and said sample-code-receiving surface is raised such that all of said code-receiving surfaces are disposed in substantially the same plane, and wherein said rack further defines openings to allow for the passage of test radiation through at least said plurality of reagent containers to make photometric measurements.

5. The kit of claim 4, wherein said reagent codes are placed on closures of said reagent containers.

* * * * *